[19] United States Patent
Craelius et al.

[11] Patent Number: 5,333,615
[45] Date of Patent: Aug. 2, 1994

[54] APPARATUS FOR DIGITALLY RECORDING AND ANALYZING ELECTROCARDIAL AND OTHER BIOELECTRIC SIGNALS

[76] Inventors: William Craelius; Nicki A. Newby, both of 13 Cortland Dr., Somerset, N.J. 08873-1713

[21] Appl. No.: 901,891

[22] Filed: Jun. 22, 1992

[51] Int. Cl.$^5$ .......................................... A61B 5/0468
[52] U.S. Cl. .................................. 128/696; 128/731; 128/733
[58] Field of Search ............... 128/710, 696, 733, 731

[56] References Cited

U.S. PATENT DOCUMENTS

| | | | |
|---|---|---|---|
| 4,193,393 | 3/1980 | Schlager | 128/710 |
| 4,506,678 | 3/1985 | Russell et al. | 128/630 |
| 4,878,498 | 11/1989 | Abrams et al. | 128/731 |
| 5,125,412 | 6/1992 | Thornton | 128/710 |
| 5,215,098 | 6/1993 | Steinhaus et al. | 128/696 |

Primary Examiner—William E. Kamm
Assistant Examiner—Scott M. Getzow
Attorney, Agent, or Firm—Plevy & Associates

[57] ABSTRACT

Apparatus for digitally recording and analyzing electrocardial and other bioelectric signals, includes a port for connecting an external measuring device; first and second differential input channels for receiving a data signal from the measuring device and for amplifying and filtering the data signal; a compression circuit for compressing the data signal from the input channels so that the compressed data signal includes only changes in amplitudes at particular points, along with a measure of elapsed time since a previous change in amplitude at the particular points, thereby omitting redundant points of the data signal; a random access memory for storing the compressed data signal; a microprocessor for controlling the storage of the compressed data signal in the memory; a power management circuit for turning power to the apparatus ON and OFF at predetermined intervals; and a position switch for indicating the position of a person wearing the apparatus relative to a vertical position.

20 Claims, 6 Drawing Sheets

APPARATUS FOR DIGITALLY RECORDING AND ANALYZING ELECTROCARDIAL AND OTHER BIOELECTRIC SIGNALS

BACKGROUND OF THE INVENTION

1. Field of the Invention

Many monitoring situations, both health and task-related, require continuous recording of vital signals in ambulatory subjects. This recording is performed in many different ways, such as with electrocardiography (ECG) and the like. For example, electrocardiographic testing during exercise remains the primary initial screening for coronary artery disease. Another diagnostic purpose of some ECG recordings is the detection of low amplitude signals occurring within the ST segment, known as late ventricular potentials (LVPs). Since these potentials may be precursors of sudden cardiac death, monitoring patients for extended periods is of diagnostic importance. Another application is the recording of heart rate for use as an indicator of the autonomic nervous system. In other applications, it is important to physiologically monitor healthy persons engaged in sensitive tasks such as aircraft piloting.

ECG signals contain information in a frequency band ranging from 0.05 Hz to at least 500 Hz. At the low frequency end, the most important portion of the ECG is the ST segment, the slope and height of which can indicate coronary perfusion. The high frequency end of the ECG spectrum may represent signals originating from discrete regions of the myocardium, the electrical conduction patterns of which are abnormal or distinct from the surrounding tissue.

In addition to the diagnostic information contained in specific frequency bands, there are also specific amplitude ranges that contain distinct diagnostic information. The low amplitude range, within approximately ±200 microvolts of the isoelectric line, contains information regarding acute ischemia, as recorded in the ST segment. Low amplitude signals also comprise the major portions of the P and T waves. Much of the diagnostic information from low amplitude signals is based on the simple presence or absence of the possible waves, and their direction with respect to the baseline. The precise shapes and sizes of the low amplitude waves are also important, and comprise the remainder of the information contained in the low amplitude signals. The highest amplitude signals of the ECG, that is, the R waves, are generally one log unit greater in amplitude than the low range, and represent the excitation of the bulk of the ventricle. The overall shape, size, and direction of the R wave provides information regarding the nature of ventricular excitation. Small amplitude signals that may be superimposed on the R wave may be of diagnostic value, but are generally not considered in standard ECG recordings.

For some diagnostic purposes, interval measurements are the primary goal. For example, heart rate variability measurements apply advanced mathematical analyses to a sequence of consecutive heart-beat intervals. The analysis depends on the sequential estimation of intervals between sinus-node activations, that correspond approximately to the occurrence of the P wave of the ECG. Since the P wave is often difficult to reliably detect, the much larger R wave is generally used as the fiducial marker of sinus node activation. The accuracy of R-R interval measurements is dependent on the method used to detect R waves. Relatively small errors in the measurement, especially if they are non-random, can be magnified by powerful mathematical analyses such as spectral analysis, leading to inaccurate diagnoses.

Another diagnostic purpose that relies heavily on interval measurement is the detection of late ventricular potentials (LVPs). The primary goal of this procedure is to detect the presence or absence of small high frequency signals following the QRS wave, and within the ST segment. Since LVPs have a signal-to-noise (S/N) ratio of less than one, averaging techniques are generally used to detect them. Since averaging must generally be used, it is important to accurately measure the occurrence of the R wave as a fiducial marker, and to measure the duration of the LVPs.

The ideal monitoring system should record and store the true signals as they change, within the entire relevant ranges of frequency and amplitude. Signal fidelity is thus of paramount importance, and it is the goal of all recording systems. However, practical recording systems, especially those that must continuously record from mobile subjects, all suffer technical limitations and therefore sacrifice some signal fidelity.

2. Description of the Prior Art

Until recently, the main options for continuous mobile recordings were either Holter monitors using magnetic tape, or radio-frequency telemetry. The disadvantages of the Holter method include its relative bulk, distortion from tape artifacts, inflexibility, and the necessity for reading and analyzing the tape using a specialized computer. Telemetry can be less bulky, but requires the proximity of a receiver-recorder.

The primary technical hurdle that must be overcome for silicon data recorders is adequate compression of data, without loss of significant information. Real-time continuous (24 hour) recording of signals on present-day silicon requires substantial data compression. For example, with 4 megabytes of silicon memory, an upper data rate of approximately 200 bits per second for each of 2 ECG channels can be stored. Since the sample rate recommended by the American Heart Association for ECG is 250 samples per second (8 bits per sample), a data compression factor of 10:1 would be required.

Several data compression techniques have been developed specifically for the ECG. These techniques are all based on mathematical algorithms that operate on data samples obtained at fixed sampling rates by a conventional analog to digital converter. Each data compression method can be quantified by two numbers, the compression ratio (CR) consisting of the number of incoming bits divided by the number of bits stored, and the percent root distortion (PRD), a measure of the amount of signal distortion caused by the compression. CR is monotonically related to PRD. Published values of CR range from 3 to 10, with PRD values ranging from 1 to 20, for various algorithms. Since the CR is relatively fixed for a given algorithm, a necessary strategy is to set the data sampling rate as low as possible in order to reduce the total amount of data.

Standard analog to digital conversion uses a signal level approximator which stores the current signal amplitude. This amplitude is read and stored at fixed intervals.

Data compression algorithms operate by identifying certain samples in the stored data array that are "redundant" and hence can be discarded. For electrocardiographic type signals, a sample is considered redundant if the possible amplitude values of the quantized signal are not equally probable. The redundant point need not be stored, since its value can be predicted (with some uncertainty) by the proximal points.

In general, the algorithms include two stages: compression and reconstruction. Compression is achieved by scanning each data sample and deciding, in comparison with adjacent samples using pre-defined criteria, whether or not the sample is redundant. The redundant points are thrown away without possibility of recovery, and thus the process is irreversible. The reconstruction stage uses a separate algorithm to interpolate samples back into the sample array, when it is being sent to an output device, such as a printer. The fidelity of the reconstructed signal is thus algorithm-dependent, and distortions are a necessary by-product. Algorithms differ with respect to the specific criteria used.

The amount of compression achieved (and the corresponding distortion) by a given algorithm can be controlled by parameter adjustment. It is important that the CR be sufficiently large to store the desired time epoch of the signal, and that the PRD is small enough to ensure adequate reconstruction. Since the algorithms operate from an automatic computer program, the CR and PRD values may not be entirely predictable, and therefore it is useful to monitor these values periodically during data collection. This is done by comparison of segments of reconstructed signals with the original data, while making necessary parameter adjustments.

A secondary type of data compression is used in some systems that involves beat classification. In this method, the waveform of each incoming cardiac cycle is compared with reference cycles, and if there are no significant differences, the beat is classified as the corresponding reference type. Thus, the only data stored for that cycle is the beat type and its time of occurrence.

Existing digital data storage apparatus use algorithms of the type listed above. They therefore suffer major disadvantages. One disadvantage is processing overhead, representing several instruction cycles per data point as data are either stored or discarded. Thus, considerable CPU time is devoted to the sampling and compressing of the data, while other real time processing tasks, such as analysis, are neglected. A second disadvantage is signal distortion, mainly in loss of high frequency signal components. This effect results from sampling rates that are set too low in order reduce the total data input rate prior to compression. For example, the commonly used sampling rate of 250 Hz necessitates anti-alias filtering with a cutoff of 125 Hz. Thus, potentially valuable higher frequency components are lost. A third disadvantage is that the algorithms require continual feedback and adjustment during data collection for effective operation. A fourth disadvantage is that standard compression methods will remove data points that are indistinguishable from noise in real time. Thus, the likelihood that small signals such as LVPs can be recorded with prior art is small.

Apparatus and methods related to the present invention are disclosed in U.S. Pat. No. 4,211,238 to Shu & Squires, U.S. Pat. No. 4,193,393, U.S. Pat. No. 4,799,165 to Hollister et al. and U.S. Pat. No. 4,624,263 to Slavin.

OBJECTS AND SUMMARY OF THE INVENTION

Accordingly, it is an object of the present invention to provide an apparatus for digitally recording and analyzing electrocardial and other bioelectric signals that overcomes the problems with known arrangements.

It is another object of the present invention to provide an apparatus for digitally recording and analyzing electrocardial and other bioelectric signals in which data compression is performed in real-time, using hardware that demands zero processor time.

It is still another object of the present invention to provide an apparatus for digitally recording and analyzing electrocardial and other bioelectric signals which does not require removal of redundant points, since redundant points are omitted during the data compression.

It is yet another object of the present invention to provide an apparatus for digitally recording and analyzing electrocardial and other bioelectric signals in which an adaptive sampling operation is used, so that the effective frequency response is at least an order of magnitude greater than existing apparatus.

It is a further object of the present invention to provide an apparatus for digitally recording and analyzing electrocardial and other bioelectric signals in which, since no sampled data points are discarded, continual feedback is not required for effective operation.

It is a still further object of the present invention to provide an apparatus for digitally recording and analyzing electrocardial and other bioelectric signals which is better than known apparatus with respect to interval measurements, including both P-P and R-R intervals.

It is a yet further object of the present invention to provide an apparatus for digitally recording and analyzing electrocardial and other bioelectric signals in which the ability to detect LVPs is enhanced.

It is another object of the present invention to provide an apparatus for digitally recording and analyzing electrocardial and other bioelectric signals in which there is extreme flexibility afforded by user programmability.

It is still another object of the present invention to provide an apparatus for digitally recording and analyzing electrocardial and other bioelectric signals in which the user can program for several options, including but not limited to:

1) continuous sampling and storing of signals,
2) specification of one or two channels,
3) storing of only intervals between cycles (that is, heartbeats or muscle contractions),
4) storage of certain types of signals, using a beat classification scheme,
5) sampling and storing only at pre-selected intervals, such as by the minute, hour, and the like, and
6) operation control by remote telephone.

It is yet another object of the present invention to provide an apparatus for digitally recording and analyzing electrocardial and other bioelectric signals which draws less power than conventional methods of analog to digital conversion.

It is a further object of the present invention to provide an apparatus for digitally recording and analyzing electrocardial and other bioelectric signals, having a permanently powered operation, wherein power management and timing components can turn on and off power to the apparatus at predetermined intervals.

In accordance with the present invention, a microprocessor based apparatus is provided for monitoring and recording electrocardial and other bioelectric signals and uploading the stored signals to a computer for processing and analysis. The apparatus features reversible level time coded data compression and the ability to configure the apparatus for various applications through the computer interface. As a result, large amounts of clinically relevant ECG data can be stored, because of the data compression operation, which relies on the fact that there are certain ranges of signal amplitude wherein major portions of diagnostic information are concentrated.

The apparatus includes two differential input channels for analog data. Both or only one input channel may be used, depending upon the application. Either or both channels may be used, in any combination, for electrocardial signals, respiration, temperature, blood pressure measurements, or other types of low voltage analog electrical signals. Gain adjustment is under the control of the microprocessor in accordance with the software therein, and bandwidth is controlled by changing two hardware components. Also included is a mercury switch which can be used as an indicator of the static position with respect to vertical and of certain forms of motion.

The user interface is flexible and simple. There is a push button on the apparatus which can be actuated by the user to start the recording session, or to signal and record an event. The apparatus can be programmed to begin sampling at predetermined intervals, or it can signal the user regarding predetermined or ongoing conditions, via a beeper.

Alternatively, the apparatus can be controlled by serial communication from a remote location. Control includes turning on and off the circuitry, and modes of data sampling.

The goal of the invention is to offer an improved apparatus for digital recording of waveforms. The specific application contemplated is the recording of ECG waveforms, with special emphasis on accurately measuring temporal relationships among their specific components. In this regard, the advantage of the present apparatus over the prior art is its greater accuracy in measuring the timing between specific occurrences in the cardiac cycle. Prior art, by using fixed rate sampling followed by compression, suffers much loss in temporal accuracy. In contrast to prior art, the present invention measures and stores with a high degree of accuracy the time that the signal reaches specific amplitudes. Since specific amplitudes can often be associated with specific cardiac events, such as the excitation of a defined region of the atrium or ventricle, precise knowledge of their timing is useful. Specifically, the measurement of intervals, such as P-R, S-T and R-R, can be made highly accurate. Another interval measurement that can be accurately made is the duration of LVPs, should they be present.

In accordance with an aspect of the present invention, apparatus for digitally recording and analyzing electrocardial and other bioelectric signals, includes port means for connecting an external measuring device; input channel means for receiving a data signal from the measuring device; compression circuit means for compressing the data signal from the input channel means so that the compressed data signal includes only changes in amplitudes at particular points, along with a measure of elapsed time since a previous change in amplitude at the particular points; memory means for storing the compressed data signal; and microprocessor means for controlling the storage of the compressed data signal in the memory means.

Specifically, the input channel means includes first and second differential input channels for processing the data signal. Each differential input channel includes means for eliminating baseline drift, followed by low pass filter means for filtering the data signal, and followed by variable gain amplifier means for amplifying the data signal and gain control means for adjusting the gain of the variable gain amplifier means for optimal feature detection in response to the microprocessor means.

The apparatus further includes position switch means for indicating the position of a person wearing the apparatus relative to a vertical position.

The apparatus further includes comparator means for detecting voltage ranges in the data signal for each channel, the comparator means being connected to the microprocessor means such that the range value may be stored in the memory means each time there is a change in the range value for any channel.

The apparatus further includes data timer means within the microprocessor means such that the number of data timer cycles since the last change in the range value may be stored in the memory means together with the range value each time there is a change.

The above and other objects, features and advantages of the invention will become readily apparent from the following detailed description thereof which is to be read in connection with the accompanying drawings.

DETAILED DESCRIPTION OF A PREFERRED EMBODIMENT

Figure 1:
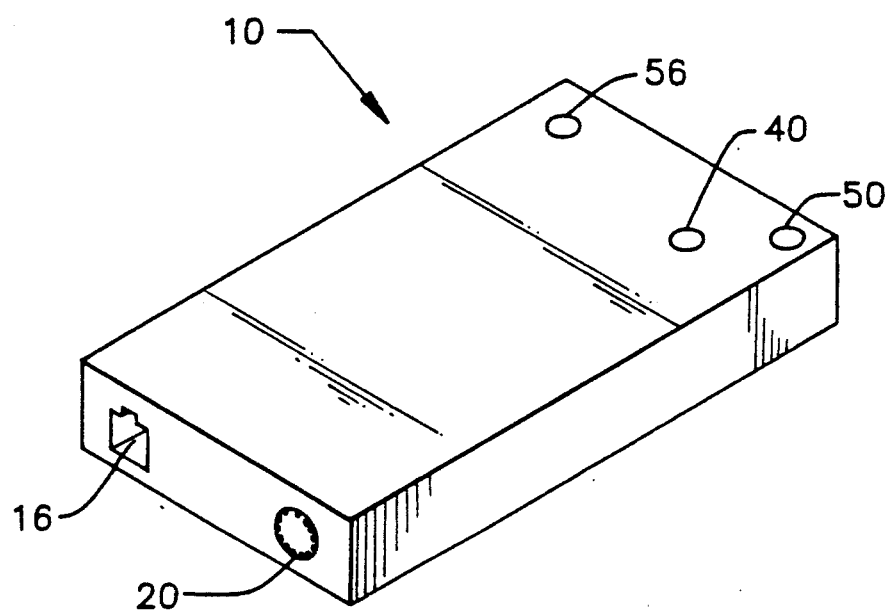
FIG. 1 is a perspective view of apparatus for digitally recording and analyzing electrocardial and other bioelectric signals, according to the present invention.
Figure 2:
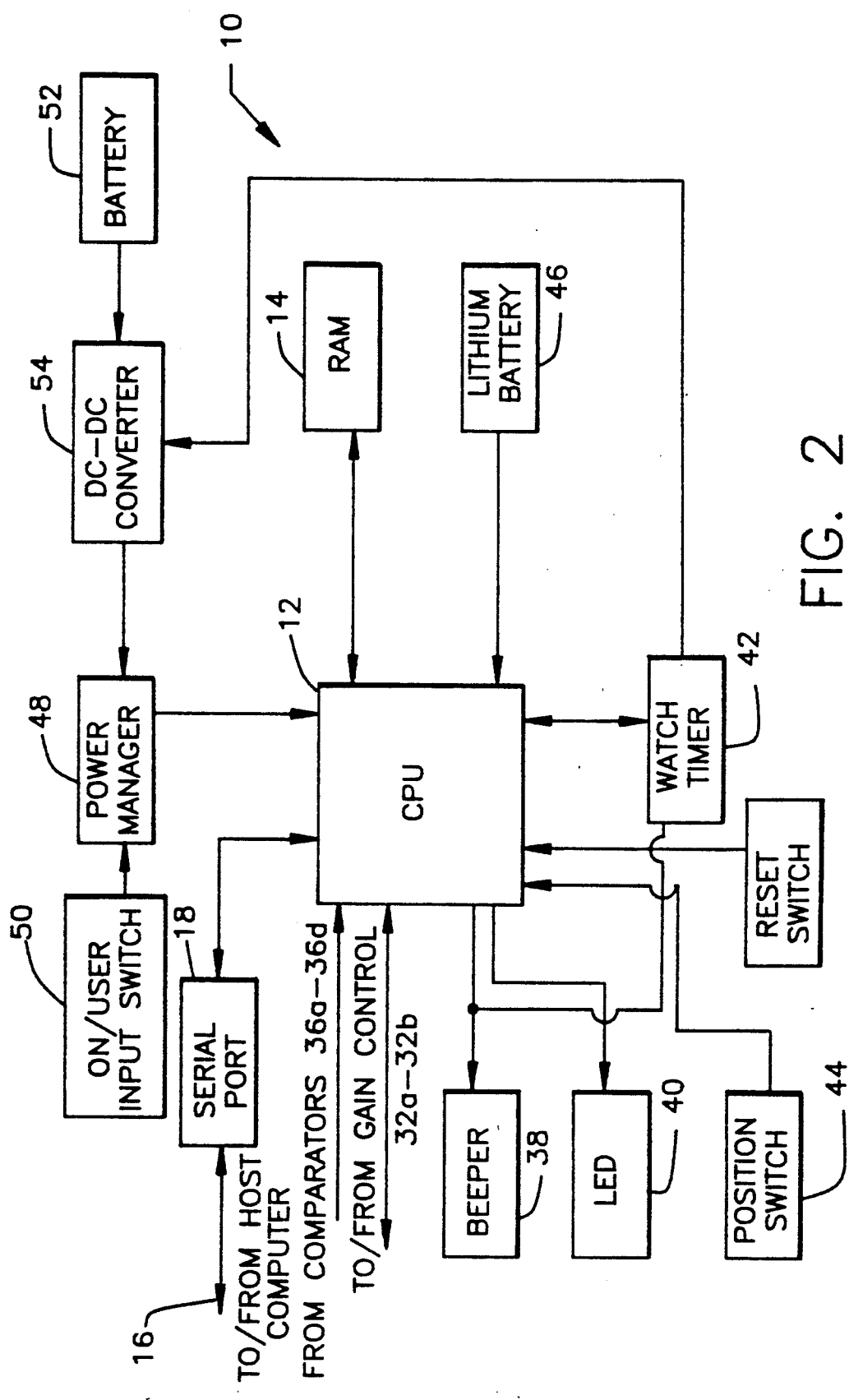
FIG. 2 is a block diagram of the data processing and storage portion of the apparatus of FIG. 1.
Figure 3:
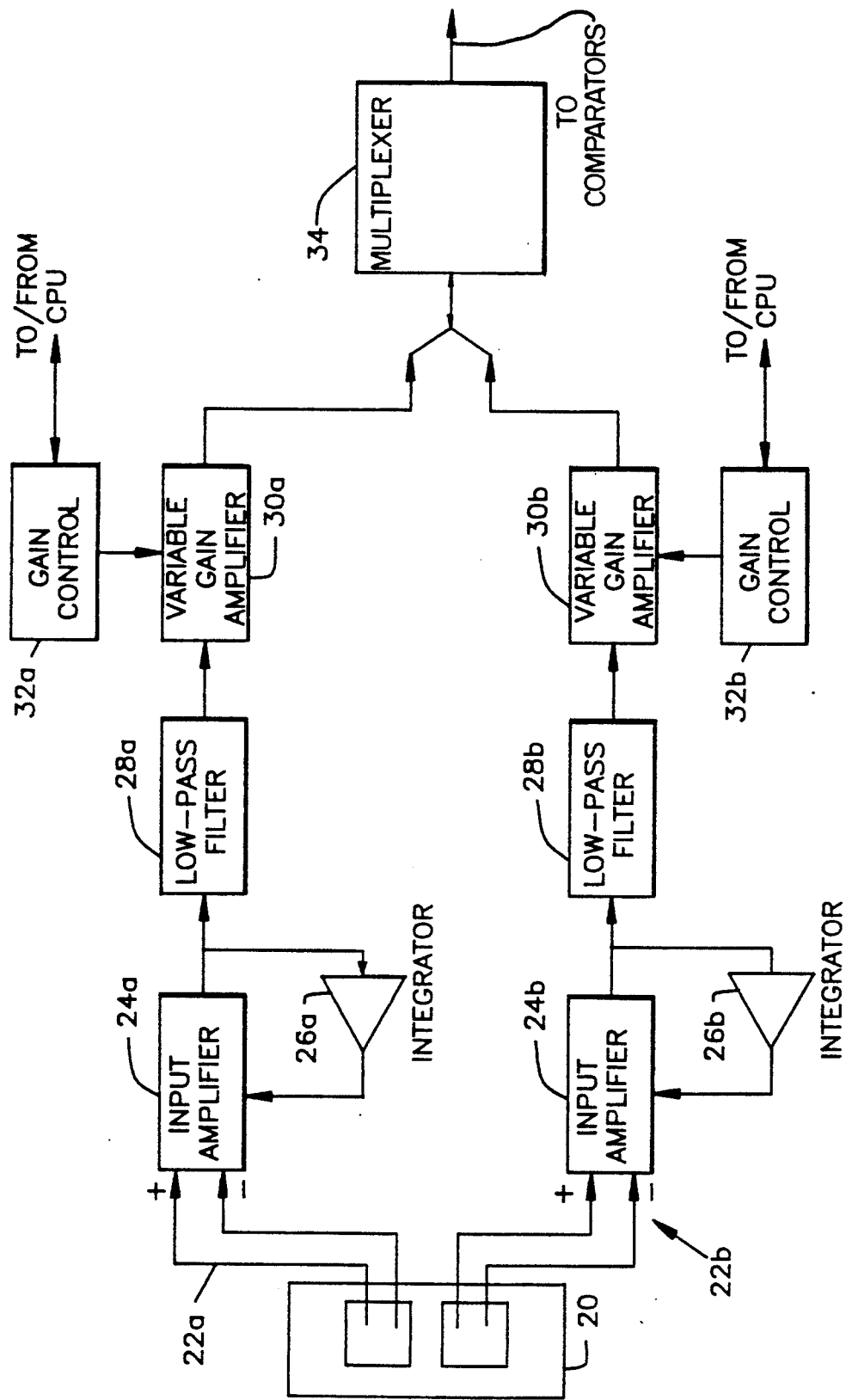
FIG. 3 is a block diagram of the input stage of the apparatus of FIG. 1.
Figure 4:
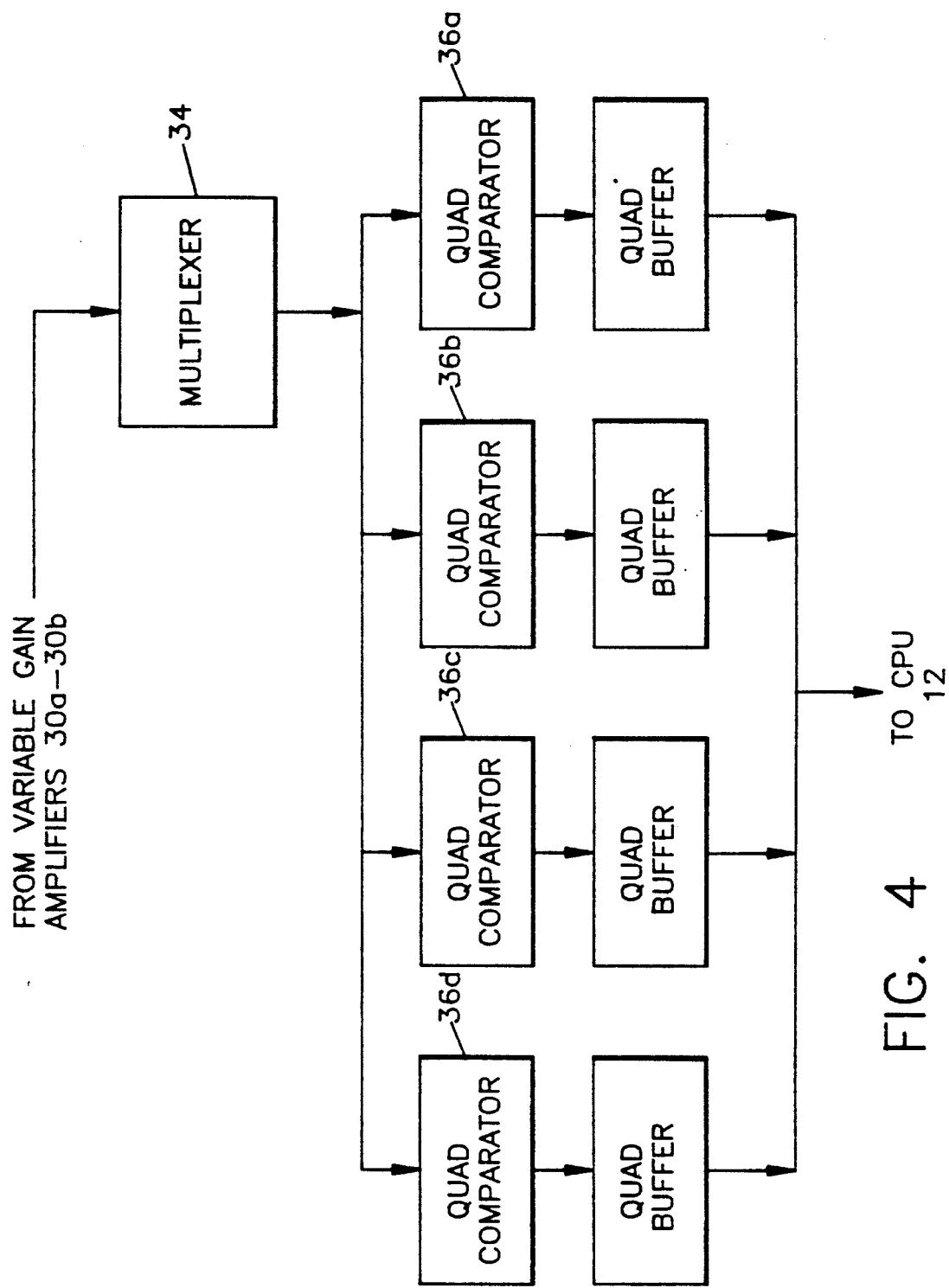
FIG. 4 is a block diagram of the comparator stage of the apparatus of FIG. 1.

Referring to FIGS. 1–4, an apparatus 10 for digitally recording and analyzing electrocardial and other bioelectric signals, includes a microprocessor or central processing unit (CPU) 12 for controlling the various operations and a random access memory (RAM) 14 for storing a program that includes a variety of routines that allows CPU 12 to perform various types of data collection. Thus, the program is run in accordance with instructions from a user, whereby the program requests certain information from the user.

As will be appreciated from the discussion which follows, apparatus 10 is connected to a host computer (not shown) through a suitable cable having a serial DIN connector (not shown) at one end which plugs into the host computer and with an RJ-11 or similar telephone-type jack (not shown) that plugs into an RJ-11 port 16. Port 16 is connected to CPU 12 through a serial port 18.

Apparatus 10 has three basic operational modes: (1) a configuration mode, (2) an upload mode and (3) a data collection mode. The software resident in the host computer has corresponding modules to interface with apparatus 10 in the configuration and uploading modes. In addition, the host computer software has an analysis mode. In the data collection mode, apparatus 10 operates independently of the host computer. On the other hand, in an analysis mode, the host computer operates independently of apparatus 10.

Before performing any operation, apparatus 10 must be configured. Thus, apparatus 10 must be connected to the host computer via port 16, and the user must run the computer program that interfaces with apparatus 10. If an apparatus 10 which contains no data is connected to the host computer, the host computer forces the user to select the configuration mode which will then be set for both the host computer and apparatus 10.

In the configuration mode, the host computer presents the user with options for data collection and other choices. Some collection modes may require additional information from the user, such as when to start collecting data, at what intervals, and for how long. In the configuration mode, it is possible to send data to apparatus 10 that will identify who will be operating apparatus 10, the data, and the like. After the configuration is completed, apparatus 10 may be disconnected from the host computer and will operate independently from it.

If an apparatus 10 is connected which contains stored data, the user will be forced to select the download mode for the host computer. Apparatus 10 will then enter the upload mode, whereby data will then be sent from apparatus 10 to the host computer. The host computer will allow the user to specify where the data is to be stored and to enter information identifying the data and the relevant circumstances regarding its collection. After data has been downloaded, the user will be allowed to enter the configuration mode to reconfigure apparatus 10 for new data collection sessions.

If an apparatus 10 is not connected, or if data has already been downloaded from a connected device, the user will enter the analysis mode. Various mathematical routines are available in the analysis mode with which stored data can be reconstructed, displayed on the computer monitor, printed on paper, or analyzed.

The software program resident in apparatus 10 operates in the following manner. When apparatus 10 is powered ON, the software program attempts to communicate with the corresponding host computer program described above. If communication is successful, apparatus 10 will be under the control of the host computer. Data can then be uploaded and/or the apparatus can be configured for a new session, as described above. After data has been successfully uploaded, stored data may be cleared from RAM 14 to make room for new data. It is not possible to configure apparatus 10 or clear data from RAM 14 unless previously existing data has been successfully uploaded. This is a protection against accidental erasure and loss of data.

If apparatus 10 does not establish communication with the host computer program, apparatus 10 automatically enters the data collection mode and will collect data according to whatever procedures are contained within its program and the configuration data previously supplied by the operator.

In the data collection mode, input transducers (not shown), such as ECG electrodes, microphones, temperature probes, strain gauges, and the like, are connected to an input connector 20. Apparatus 10 includes two input channels 22a and 22b which connect to connector 20, each input channel 22a and 22b being differential, with a separate ground lead.

Input channels 22a and 22b receive the respective data from input connector 20 and supply the same to respective input amplifiers 24a and 24b, which are high input impedance differential operational amplifiers with a common mode rejection ratio exceeding 120 dB. To eliminate baseline drift, without the disadvantage of high pass filtering, a voltage-clamp arrangement 26a and 26b, respectively, is used in a feedback path with the respective input amplifier 24a and 24b. In effect, each voltage-clamp arrangement 26a and 26b functions as an integrator, with a portion of the output of the each amplifier 24a and 24b being fed back through the respective integrator 26a and 26b to the reference input of the same amplifier 24a and 24b. The time constant of the integrator determines the low frequency response, which is linear down to 0.05 Hz.

Following the respective input amplifier 24a and 24b, each channel 22a and 22b includes a low-pass filter 28a and 28b, respectively. Preferably, each low-pass filter 28a and 28b has a −3 dB cutoff of 500 Hz. Thus, the bandwidth exceeds the American Heart Association recommendation.

A variable gain amplifier 30a and 30b is connected to the output of each respective low-pass filter 28a and 28b. The gain of amplifiers 30a and 30b is controlled by gain control circuits 32a and 32b, respectively, which are formed as digital potentiometers. Gain control circuits 32a and 32b are, in turn, each independently controlled by CPU 12, and automatically adjusted for optimal feature detection. The total gain of each variable gain amplifier 30a and 30b preferably ranges from 8,000 to 20,000.

Following the input amplification stage, the signals from each channel 22a and 22b are supplied to a multiplexer 34 from which they are directed through a single output line to a series of comparators 36a–36d. Comparators 36a–36d provide for powerful data compression while allowing high-fidelity reconstruction of the signal. The method of analog to digital conversion obtained with the use of comparators 36a–36d differs from that commonly used in several respects. The present method allows detection of a limited number of voltage ranges and, rather than storing the value at fixed intervals, stores or detects only changes in values or amplitudes, together with a measure of elapsed time since the previous change.

Comparators 36a–36d are set to detect different voltage levels of the amplified signal. Half of comparators 36a–36d are set to detect various levels of negative signals, the other half to detect positive signals. If two channels are being used, comparators 36a–36d are continuously switched from one channel to the other so that the signals are sampled alternately. A data timer within CPU 12 is set to tick at a fixed rate and is reset to zero each time a change in signal amplitude is detected.

Each comparator 36a–36d acts as a trigger to detect voltages exceeding a certain level. Comparators 36a–36d are set so that level one detects the most negative voltages and level N (where there are N comparators) detects the most positive voltages. With N comparators, N+1 voltage ranges can be discerned. For example, with 16 comparators, there are 17 voltage ranges. The zero voltage level falls between the two middle comparators.

CPU 12 continuously monitors comparators 36a–36d, checks for data integrity and records pertinent data. Because of the arrangement of comparators 36a–36d, any one comparator can only be triggered if all the lower level comparators are also triggered. If CPU 12 detects that this is not the case, an error condition exists.

If automatic corrections do not work, a warning signal can be sent to the user. This can be accomplished with a series of beeping sounds by actuating a beeper 38 or by a flashing light emitting diode (LED) 40.

Each time a change in comparator configuration is detected for any channel, the range value and the number of data timer cycles since the last change are stored in RAM 14. This is accomplished via a data timer within CPU 12. If eight comparators are used, 4 bits are needed to store the range value, and if 16 comparators are used, 5 bits are needed. If two channels are being used, the channel is designated as a single bit. The number of data timer cycles since the last change is a compressed measure of elapsed time. For instance, if data timer is set to trigger at intervals of 1 msec., and 150 msec. has elapsed since the previous change, the value 150 will be stored. After the data timer value is stored, the data timer is reset to zero. The rate at which data timer runs can be adjusted by the software according to the requirements of the application. This method of data storage is thus very conservative of RAM space.

Apparatus 10 further includes a mercury switch 44 which functions as a position switch. Mercury switch 44 is oriented in apparatus 10 such that when the patient is wearing apparatus 10 in the prescribed manner, switch 44 will detect certain positions and movements of the patient. If the patient is standing erect, mercury switch 44 will be OFF. If the patient is in a prone position, the switch will be ON. If the patient is engaged in certain types of exercise, for instance jogging or exercises requiring bending movements, the switch will alternate between an ON and OFF position. Switch 44 is connected to CPU 12, and the value of switch 44 can be stored in RAM 14, as required, as a single bit.

It will be appreciated that the comparator levels determine the dynamic range, as well as the resolution, of the sampling system. For ECG signals it is important to have high resolution near the baseline, while maintaining sufficient dynamic range to record the highest amplitude signals. A useful arrangement of levels for ECG sampling is thus an exponential range, since the information content of signals increases as the logarithm of the signal amplitude. The latter statement was proven by the Shannon-Hartley Law:

$$C = W^*(1 + \log S/N),$$

where C represents the information transfer rate of a signal, W is the bandwidth of the signal, and S/N is the signal-to-noise ratio of the signal.

Thus, the information content of a signal increases as the logarithm of its signal-to-noise ratio plus 1. Exponential quantization steps therefore provide a resolution that is directly related to the information content of the signal, assuming that the baseline is close to the zero level. This means that resolution of signal would be highest for the lowest amplitude range, and decreases exponentially with increasing amplitude.

The comparator levels of the present invention are set to be symmetrical about zero voltage. An example of quantization steps is given by the following formula:

$$\text{level}(1) - \text{level}(-1) = \exp(k) - \exp(0)$$

$$\text{level}(i) - \text{level}(i-1) = \exp(\text{abs}(i)^*k) - \exp(\text{abs}(i-1)^*k),$$

for $i = 2$ to 8 and $i = -2$ to $-8$, where i is the comparator number relative to zero, level(i) is the voltage level of the comparator, and k is a constant. For a value $k = 0.30$, this yields the following information for the positive portion of the signal:

| Comparator Number | Trigger Voltage Level |
| --- | --- |
| +1 | +0.175 |
| +2 | +0.650 |
| +3 | +1.285 |
| +4 | +2.145 |
| +5 | +3.307 |
| +6 | +4.875 |
| +7 | +6.991 |
| +8 | +9.848 |

The comparators for the negative portion of the signal would be equal but opposite in sign to the above levels.

With comparators 36a-36d configured as above, the signal voltage ranges are designated as follows, assuming a gain of 10,000:

| Range Number | Voltage Range (microvolts) |
| --- | --- |
| 0 | < −985 |
| 1 | −985 to −699 |
| 2 | −699 to −487 |
| 3 | −487 to −331 |
| 4 | −331 to −215 |
| 5 | −215 to −128 |
| 6 | −128 to −65 |
| 7 | −65 to −17 |
| 8 | −17 to +17 |
| 9 | +17 to +65 |
| 10 | +65 to +128 |
| 11 | +128 to +215 |
| 12 | +215 to +331 |
| 13 | +331 to +487 |
| 14 | +487 to +699 |
| 15 | +699 to +985 |
| 16 | > +985 |

For instance, if the voltage is −200 microvolts, all the comparators from −8 through −4 would be triggered, but no others. The software in CPU 12 assigns a range value of 5 to this value. If the voltage is −1000 microvolts, no comparators would be triggered. This condition is designated as a range value of 0.

With this arrangement, the resolution of low level signals (±128 microvolts) ranges between 35 and 60 microvolts, comparing favorably with the recommendation of the American Heart Association. The dynamic range is thus sufficient to record small waves such as the P wave, and large waves such as the R wave.

If higher resolution is desired, the following method can be used, and is restricted to one channel operation. Specifically, the resolution can be improved by increasing the gain, without saturating the high level signals by splitting the signal to both amplifiers 24a and 24b. One amplifier would be adjusted to maximum gain to quantize the low level signals, while the other amplifier is set at a lower gain to quantize the large signals.

Alternative quantization methods may be chosen based on the amount of data compression achieved for specific ECG signals. For example, evenly spaced quantization levels may provide the highest compression ratio without significant loss of information.

Since CPU 12 can be used for real-time analysis, some modes of operation allow on-line classification of the beat-type. In this mode, a library of reference cardiac cycles is created during the initialization phase. Thereafter, each incoming cardiac cycle is compared with the reference library, and either classified or added to the library. In this way, a long-term record of heart rate, plus waveforms of classified beats, can be obtained.

To maximally conserve battery power and available memory, apparatus 10 is normally maintained in a waiting state, with only ultra-low level battery power being applied to watch timer 42, to serial port 18, to a power manager 48, and to RAM 14. Power distribution to separate circuits on the apparatus is controlled by power manager 48. Certain specified events can power some or all of the remaining circuitry of apparatus 10. The specified events include serial signals applied to serial port 18, activation of the user ON switch 50, or signals from watcher timer 42.

Apparatus 10 may be powered on manually, by the user, or automatically using watch timer 42. If apparatus 10 is powered on by user ON switch 50, power manager 48 applies power to CPU 12, which then signals power manager 48 to apply power to the analog circuitry. CPU 12 can then read the date and time of day from the watch timer 42 and record this data in RAM 14.

Automatic data collection of the timing operates as follows. At certain times, predetermined by the configuration module of the setup program, timer 42 sends a pulse to power manager 48, indicating the need for system operation. Power manager 48 then applies power to CPU 12, which then signals power manager 48 to apply power to the analog circuitry. Data can then be taken within 1 millisecond after signalling by timer 42. After a predetermined period of data collection, timer 42 signals power manager 48 to turn off power to all circuits. Then, apparatus 10 is returned to its waiting state, with only lithium power from battery 46 applied to timer 42, power manager 48 and RAM 14.

Automatic operation allows the user to record during certain times of day that may be of special interest, thus conserving battery and memory. Additionally, if incoming data are determined to be inappropriate or in error due to faulty inputs, circuits are shutdown, and beeper 38 is activated to send a beeper signal. Timer 42 provides accurate time and date stamps on all data.

Conditions of weak battery are signalled to the subject via beeper 38. The operation is as follows. When the voltage of the normally used battery 52 which is applied to CPU 12 through a DC-DC converter 54, drops below 4.5 volts, a pin from CPU 12 drops from logic high to logic low, and this signals timer 42 to emit a signal to the subject. At the same time, orderly shutdown of CPU 12 (Power Down Reset) begins. When a new battery 52 is inserted, operation will continue as previously once a reset switch 56 is actuated.

Figure 5:
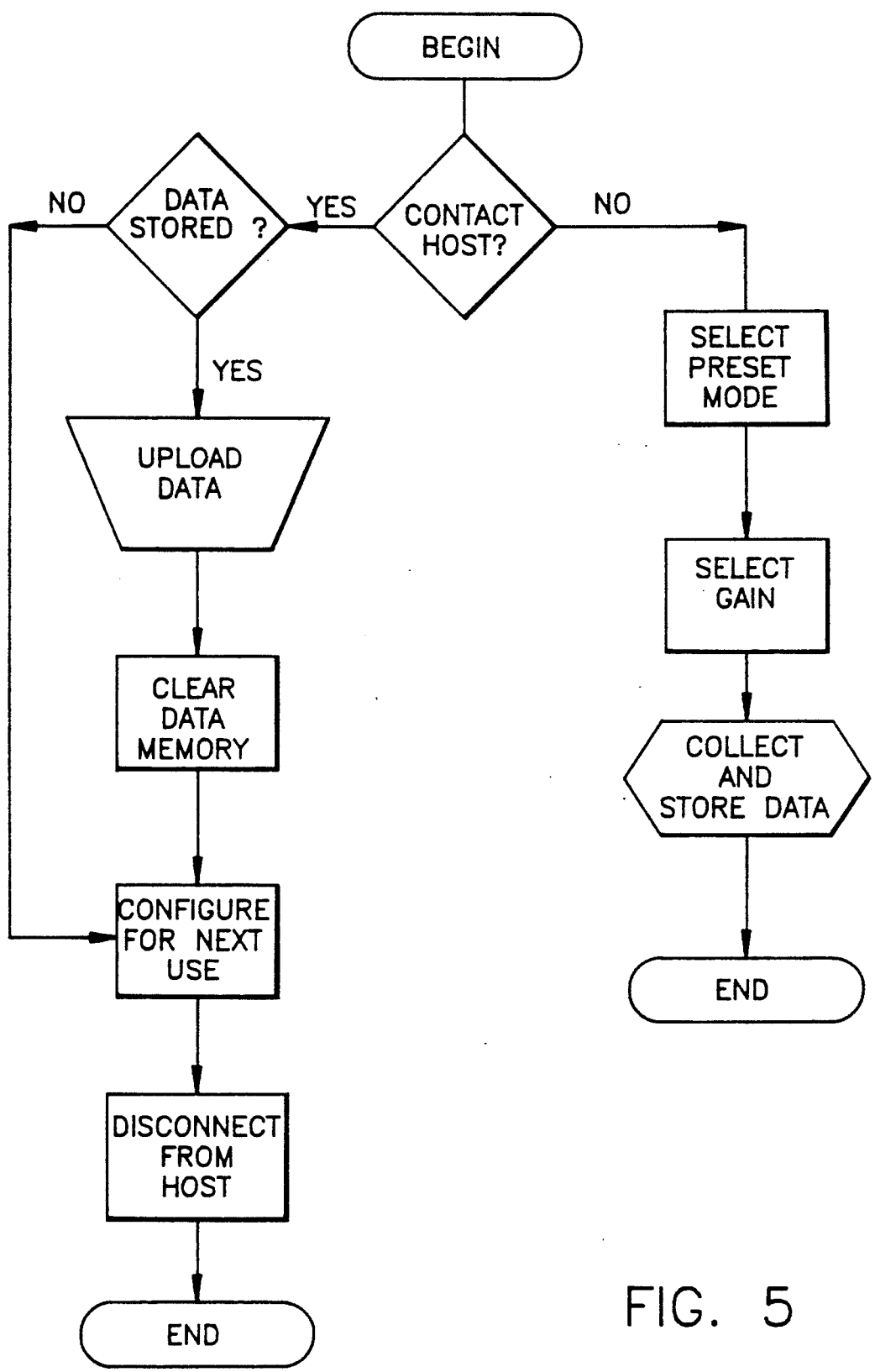
FIGS. 5 and 6 are flow charts depicting operation of the CPU.
Figure 6:
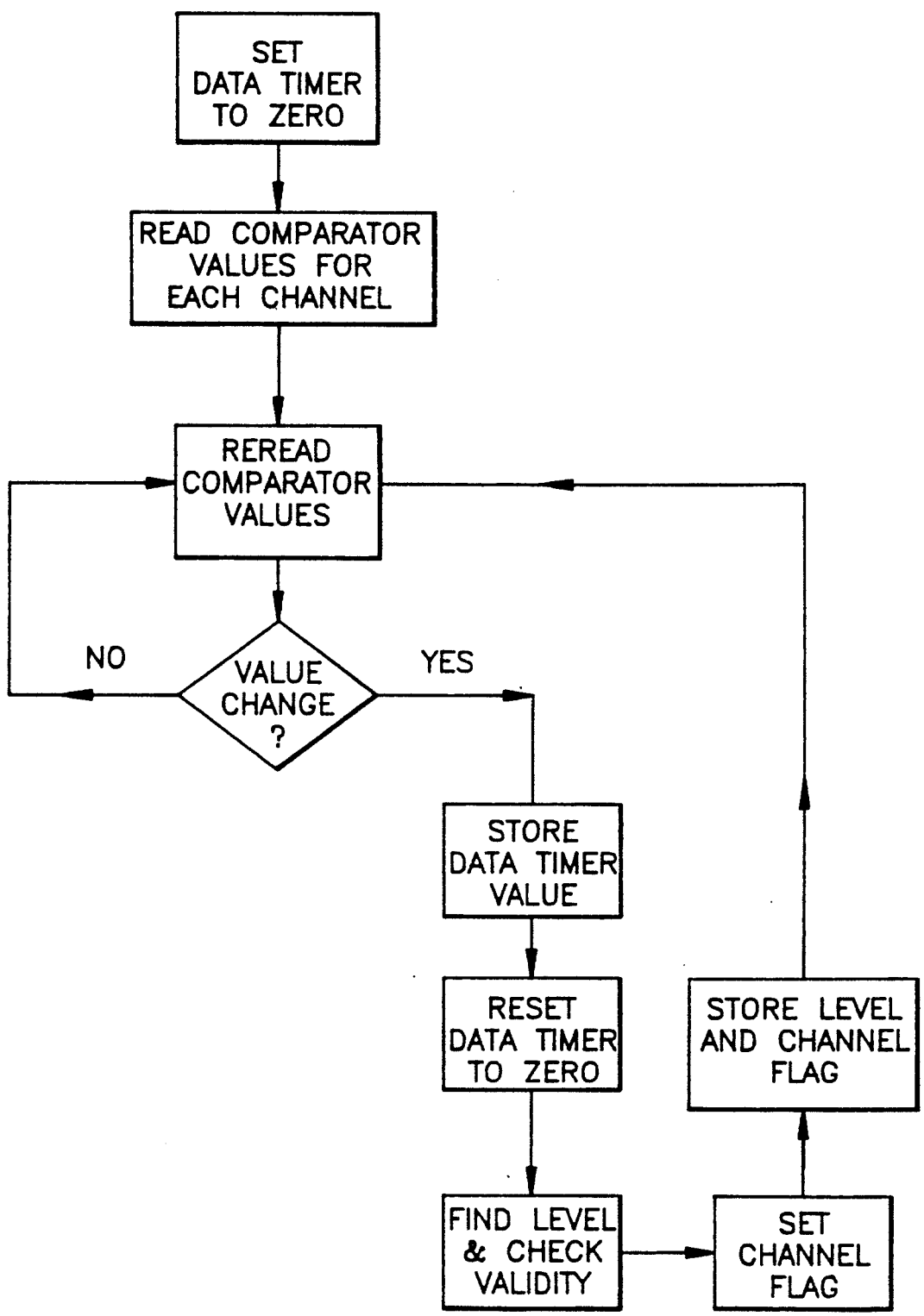

Referring to FIGS. 5 and 6, there is shown a flow chart of CPU operation.

BEGIN: Apparatus 10 is turned on or reset to start at the beginning of the program. If communication with a host computer is desired, the apparatus 10 will have been connected to the computer via a serial cable plugged into port 16 prior to this. In this case, the program on the host computer is started just after the apparatus 10 is turned on or reset.

CONTACT HOST: The program attempts to read a predetermined code entering the serial port 18. If the host computer is connected, and the computer program is running, the host computer will transmit this predetermined code out its serial port so that it will be available for the serial port 18 of apparatus 10 to read via the CPU 12. The program attempts to read this code repeatedly for a fixed period of time. If this code is read successfully, "contact host" is true. If the code is not read, "contact host" is false. If the host is contacted, additional codes may be transferred between the apparatus 10 and the host computer to verify communication.

DATA STORED: The program checks an area of memory, RAM 14, that indicates whether or not data has been stored in memory 14. This returns a true or false result, which is relayed to the host computer.

UPLOAD DATA: The program on the host computer enters "Download" mode and forces the program in the CPU 12 of the apparatus 10 to enter "Upload" mode. The program then reads the configuration data, previously stored in RAM 14, to determine what type of data is present. This information is sent to the host computer. The program then reads from RAM 14 the amount of data present and sends this information to the host computer. The actual data is then sent from RAM 14 via the CPU 12 to the host computer. The host computer prompts the user for information on how to identify and store the data and then stores it on a disk or other permanent storage medium. At this stage, the data may be rechecked against that present in RAM 14 of the apparatus 10 to be sure there were no errors in the transfer process.

CLEAR DATA MEMORY: The data memory area of RAM 14 on the apparatus 10 is reset to all zeros so that no data remains. Memory containing information on the amount of data present is also cleared to zero.

CONFIGURE FOR NEXT USE: The program on the host computer prompts the user to indicate which available data collection mode is desired for the next use of the apparatus 10. The user enters this information and it is sent via the serial port 18 to the CPU 12 which in turn stores this information in RAM 14. Additional information for identifying the user/patient, the data, etc. may also be entered at this time, sent to the CPU 12 and saved in RAM 14.

DISCONNECT FROM HOST: The programs on both the host computer and the apparatus 10 come to their respective end points and stop processing. The cable connected to the serial port of the host computer is unplugged from port 16 and may, if desired, be unplugged from the host computer as well.

SELECT PRESET MODE: The program in the CPU 12 of the apparatus 10 reads the configuration information from memory (RAM 14). According to this information a subroutine that is part of the program is selected and variable parameters may be set.

SELECT GAIN: Incoming data from the comparators 36a-d is monitored by the program in the CPU 12 apparatus 10. Depending on the data that is received, the CPU 12 may increase or decrease the gain by sending data to the gain control 32a-b. This process of monitoring the data from the comparators 36a-d and adjusting the gain control 32a-b is repeated until the data satisfy some previously defined criteria which is dependent upon the data collection mode selected. This process assumes that suitable input transducers are connected to input connector 20 and that the input transducers are connected to a suitable signal source. If no data is detected at any reasonable gains over a suitable period of time, the CPU 12 can then signal an error condition via the LED 40 or the beeper 38.

COLLECT AND STORE DATA: The data timer within the CPU 12 is reset to zero and the configuration of the comparators 36a-d is checked. Each time a change in comparators input is detected, the value of the data timer, the comparator level, and the channel (if needed) are stored in RAM 14. The data timer is then reset to zero. This process is repeated until data collection is completed.

More detail on the data collection and storage routines is contained in Flowchart 2.

The following is a program routine describing CPU operation: Program excerpts for use with APPARATUS FOR DIGITALLY RECORDING AND ANALYZING ELECTROCARDIAL AND OTHER BIOELECTRIC SIGNALS.

This procedure logs multiplexed input from two data channels using 8 comparators.

The time interval between changes in P1 (comparator input), the channel number, and the number of bits set are stored.

The time interval is stored in the first byte, the channel number in the high bit of the next byte and the number of bits set in bits 0-3.

P1 is the input from the comparators.

R3 (register bank 0) is the data timer. It is reset after each change and incremented by timer 0 to get the interval.

Channel 0 uses register bank 1.

Channel 1 uses register bank 2.

R4 stores the value of P1 previously stored.

R5 stores the number of bits set, which equals the level.

Channel selector is P3.4.

```
BEGIN_p:
    MOV     DPTR,#DATA
    CLR     P3.4        ; Select channel 0
    MOV     PSW,#8H     ; Register bank 1
    CALL    CHECK_FROM_LOW
    SETB    P3.4        ; Select channel 1
    MOV     PSW,#10H    ; Register bank 2
    CALL    CHECK_FROM_LOW
    CLR     P3.4        ; Select channel 0
    MOV     PSW,#8H     ; Register bank 1
RETEST:
    MOV     A,R4
    CJNE    A,P1,LOG    ; If there is a change log it
    JNB     P3.4,SET_CH1
SET_CH0:
    CLR     P3.4        ; Select channel 0
    MOV     PSW,#8H     ; Register bank 1
    CALL    DELAY
    SJMP    RETEST
SET_CH1:
    SETB    P3.4        ; Select channel 1
    MOV     PSW,#10H    ; Register bank 2
    CALL    DELAY
    SJMP    RETEST
LOG:
    PUSH    PSW
    MOV     PSW,#10
    MOV     A,R3        ; Get the value of the data timer
    MOV     R3,#0       ; Reset the data timer to zero
    POP     PSW
    MOVX    @DPTR,A     ; Store the value of the data timer
    JB      P1.4,HIGHER
    CALL    CHECK_FROM_LOW
    JMP     LOGBIT
HIGHER:
    INC     DPTR
    CALL    CHECK_END
    JZ      QUIT_P
    MOV     A,R5        ; R5 contains the level number
    JNB     P3.4,LOGIT
    ORL     A,#80H      ; If channel 1 set a flag
```

```
                        -continued
LOGIT:
    MOVX    @DPTR,A     ; Store the data
    INC     DPTR
    CALL    CHECK_END
    JZ      QUIT_P
    CALL    CHECK_END
    JZ      QUIT_P
    JNB     P3.4,SET_CH1
    JMP     SET_CH0
QUIT_P:
    CALL    STORE_END
    JMP     QUIT
CHECK_END:
    PUSH    PSW
    MOV     PSW,#10H    ; Register bank 2
    MOV     R6,DPL
    MOV     R7,DPH
    MOV     A,#HIGH(HIMEM); Make sure we don't
                          try to write past
    SUBB    A,DPH         ; the end of memory
    JNZ     NOT_END
    MOV     A,#LOW(HIMEM)
    SUBB    A,DPL
    JNZ     NOT_END
    MOV     A,#0
    JMP     CHK_END_RET
NOT_END:
    MOV     A,#1
CHK_END_RET:
    POP     PSW
    RET
STORE_END:
    PUSH    PSW
    MOV     PSW,#10H
    MOV     DPTR,#DATA_STOP ;Store next address past
                             end of DATA_STOP
    MOV     A,R6
    MOVX    @DPT,A
    INC     DPTR
    MOV     A,R7
    MOVX    @DPTR,A
    CALL    SIG_END     ; Signal the end
    POP     PSW
    RET
```

Check bit integrity starting from low bit.
Exit procedure with the level number in R5.

```
CHECK_FROM_LOW:
    PUSH    DPL
    PUSH    DPH
    MOV     R4,P1
CLN:
    CJNE    R4,#0,CLO
    MOV     R5,#0
    JMP     CL_RET
CLO:
    CJNE    R4,#1,CL1
    MOV     R5,#1
    JMP     CL_RET
CL1:
    CJNE    R4,#3,CL2
    MOV     R5,#2
    JMP     CL_RET
CL2:
    CJNE    R4,#7,CL3
    MOV     R5,#3
    JMP     CL_RET
CL3:
    CJNE    R4,#0FH,CL4
    MOV     R5,#4
    JMP     CL_RET
CL4:
    CJNE    R4,#1FH,CL5
    MOV     R5,#5
    JMP     CL_RET
CL5:
    CJNE    R4,#3FH,CL6
    MOV     R5,#6
    JMP     CL_RET
CL6:
    CJNE    R4,#7FH,CL7
    MOV     45,#7
    JMP     CL_RET
```

```
-continued
CL7:
    CJNE    R4,#0FFH,CHKL_FAULT
    MOV     R5,#8
CL_RET:
    POP     DPH
    POP     DPL
    RET
CHKL_FAULT:              ; Error in comparator values
    MOV     A,R4
    CALL    SENDHEX
    CALL    SIG_ERROR    ; Signal an error
    JMP     QUIT         ; or beeper could signal here
Check bit integrity starting from high bit.
Exit procedure with the level number in R5.
CHECK_FROM_HIGH:
    PUSH    DPL
    PUSH    DPH
    MOV     R4,P1
CH7:
    CJNE    R4,#0FFH,CH6
    MOV     R5,#8
    JMP     CH_RET
CH6:
    CJNE    R4,#7FH,CH5
    MOV     R5,#7
    JMP     CH_RET
CH5:
    CJNE    R4,#3FH,CH4
    MOV     R5,#6
    JMP     CH_RET
CH4:
    CJNE    R4,#1FH,CH3
    MOV     R5,#5
    JMP     CH_RET
CH3:
    CJNE    R4,#0FH,CH2
    MOV     R5,#4
    JMP     CH_RET
CH2:
    CJNE    R4,#07,CH1
    MOV     R5,#3
    JMP     CH_RET
CH1:
    CJNE    R4,#03,CH0
    MOV     R5,#2
    JMP     CH_RET
CH0:
    CJNE    R4,#01,CHN
    MOV     R5,#1
    JMP     CH_RET
CHN:
    CJNE    R4,#0,CHKH_FAULT
    MOV     R5,#0
CH_RET:
    POP     DPH
    POP     DPL
    RET
CHKH_FAULT:              ; Error in comparator values
    MOV     A,R4
    CALL    SENDHEX
    CALL    SIG_ERROR    ; Signal an error
    JMP     QUIT         ; or beeper could signal here.
```

Thus, with the present invention, data compression is performed in real-time, using hardware that demands zero processor time. Further, with such data compression, there is no requirement to additionally remove redundant points, since redundant points are omitted during the data compression. Still further, an adaptive sampling operation is used, so that the effective frequency response is at least an order of magnitude greater than existing apparatus. Further, since no sampled data points are discarded, continual feedback is not required for effective operation.

As a result, the present invention is better than known apparatus with respect to interval measurements, including both P-P and R-R intervals, and the ability to detect LVPs is enhanced.

There is further extreme flexibility afforded by user programmability. Thus, the user can program for several options, including continuous sampling and storing of signals, specification of one or two channels, storing of only intervals between cycles (that is, heartbeats or muscle contractions), storage of certain types of signals, using a beat classification scheme, sampling and storing only at pre-selected intervals, such as by the minute, hour, and the like, and operation control by remote telephone.

In addition, the present invention draws less power than conventional methods of analog to digital conversion. Thus, with the present invention, power management and timing components can turn on and off power to the apparatus at predetermined intervals.

Having described a specific preferred embodiment of the invention with reference to the accompanying drawings, it will be appreciated that the present invention is not limited to that precise embodiment and that various changes and modifications can be effected therein by one of ordinary skill in the art without departing from the scope or spirit of the invention as defined by the appended claims.

What is claimed is:

1. Apparatus for processing electrocardial and other bioelectric signals received from an external measuring device, comprising:

port means connectable to said external measuring device;

input channel means adapted to receive a data signal from said measuring device;

compression circuit means for compressing the data signal from said input channel means so that the compressed data signal includes only changes in amplitudes at particular points;

memory means for storing said compressed data signal; and microprocessor means for controlling the storage of said compressed data signal in said memory.

2. Apparatus according to claim 1, wherein said compression circuit means includes means for omitting redundant points of the signal supplied thereto during compression of said data signal.

3. Apparatus according to claim 1, further including power management means for turning power to said apparatus ON and OFF at predetermined intervals.

4. Apparatus according to claim 1, wherein said input channel means includes means for eliminating baseline drift.

5. Apparatus according to claim 4, wherein said means for eliminating baseline drift includes amplifier means for amplifying said data signal and integrator means for integrating the output signal from said amplifier means and for feeding back the integrated signal to an input of said amplifier means.

6. Apparatus according to claim 1, wherein said input channel means includes variable gain amplifier means for amplifying said data signal, and gain control means for adjusting the gain of said variable gain amplifier means for optimal feature detection in response to said microprocessor means.

7. Apparatus according to claim 1, wherein said input channel means include low pass filter means for filtering said data signal.

8. Apparatus according to claim 1, wherein said input channel means includes first and second differential input channels for processing said data signal.

9. Apparatus according to claim 8, wherein each said differential input channel includes means for eliminating baseline drift and high frequency noise and variable gain amplifier means responsive to said microprocessor means for adjusting the magnitude of said data signal, thereby providing.

10. Apparatus according to claim 8, further including multiplexer means for multiplexing data signals from said first and second differential input channels and for supplying a signal along a single line to said compression means.

11. Apparatus according to claim 1, further includes position switch means for indicating the position of a person wearing the apparatus relative to a vertical position.

12. Apparatus according to claim 11, wherein said position switch means includes a mercury switch.

13. Apparatus according to claim 1, further including data timer means responsive to changes in amplitude and operable to provide a measure of elapsed time from a previous change in amplitude at the particular points, said data timer means being connected with said microprocessor means such that the number of data timer cycles since the last change are stored in said memory means.

14. Apparatus according to claim 1, wherein said compression circuit means comprises a plurality of threshold detection means for detecting when the amplitude of said data signal reaches one of a plurality of predetermined levels, each respective threshold detection means defining a range of amplitude levels and being triggered when said data signal reaches a corresponding one of said predetermined levels.

15. Apparatus according to claim 1, wherein said compression circuit means comprises a plurality of threshold detection means for detecting when the amplitude of said data signal reaches one of a plurality of predetermined levels, a first of said threshold detection means defining a lowermost voltage range and each additional threshold detection means defining an incrementally higher voltage range.

16. Apparatus according to claim 15, wherein each of said threshold detection means is operable in a first operating state when the amplitude level is within its corresponding voltage range and in a second operating state when the amplitude level is outside said corresponding voltage range, wherein a change in the amplitude of said data signal is detectable when the operating state of at least one of said threshold detection means changes.

17. Apparatus according to claim 16, further including means responsive to said threshold detection means and operable to provide a measure of elapsed time since a previous change in amplitude at the particular points, said data timer means being connected with said microprocessor means such that the number of data timer cycles since the last change are stored in said memory means.

18. Apparatus according to claim 17, wherein said data timer means is adapted to register times of operating state changes by said threshold detection means and to adjust a range value and the number of data timer cycles since the last change for each change in response thereto.

19. Apparatus according to claim 15, wherein said microprocessor means is adapted to store a range voltage value when the operating state of at least one of said threshold detection means changes.

20. Apparatus for processing electrocardial and other bioelectric signals from an external measuring device, comprising:

input channel means adapted to receive a data signal from said measuring device;

compression circuit means coupled to said input channel means for compressing the data signal from said input channel means so that the compressed data signal includes only changes in amplitudes at particular points, said compression circuit means being adapted to omit redundant points of the signal supplied thereto during compression of said data signal;

memory means for storing said compressed data signal; and microprocessor means for controlling the storage of said compressed data signal in said memory means.

* * * * *